US008067033B2

(12) United States Patent
Xu et al.

(10) Patent No.: US 8,067,033 B2
(45) Date of Patent: *Nov. 29, 2011

(54) STABLE COMPOSITIONS OF FAMOTIDINE AND IBUPROFEN

(75) Inventors: Jerry Xu, Hunt Valley, MD (US); George Tidmarsh, Portola Valley, CA (US)

(73) Assignee: Horizon Pharma USA, Inc., Northbrook, IL (US)

( * ) Notice: Subject to any disclaimer, the term of this patent is extended or adjusted under 35 U.S.C. 154(b) by 529 days.

This patent is subject to a terminal disclaimer.

(21) Appl. No.: 12/324,808

(22) Filed: Nov. 26, 2008

(65) Prior Publication Data

US 2009/0142393 A1    Jun. 4, 2009

Related U.S. Application Data

(60) Provisional application No. 60/991,628, filed on Nov. 30, 2007.

(51) Int. Cl.
- *A61K 31/425* (2006.01)
- *A61K 31/19* (2006.01)
- *A61K 9/16* (2006.01)

(52) U.S. Cl. .......... 424/490; 514/370; 514/570
(58) Field of Classification Search .......... None
See application file for complete search history.

(56) References Cited

U.S. PATENT DOCUMENTS

| 4,283,408 A | 8/1981 | Hirata et al. |
|---|---|---|
| 4,757,060 A | 7/1988 | Lukacsko et al. |
| 5,037,815 A | 8/1991 | Lukacsko et al. |
| 5,120,850 A | 6/1992 | Bod et al. |
| 5,128,477 A | 7/1992 | Bod et al. |
| 5,204,118 A | 4/1993 | Goldman et al. |
| 5,364,616 A | 11/1994 | Singer et al. |
| 5,384,130 A | 1/1995 | Kamada |
| 5,417,980 A | 5/1995 | Goldman et al. |
| 5,466,436 A | 11/1995 | Stables |
| 5,496,836 A | 3/1996 | Di Rocco et al. |
| 5,505,983 A | 4/1996 | Kamada |
| 5,601,843 A | 2/1997 | Gimet et al. |
| 5,696,165 A | 12/1997 | Armitage et al. |
| 5,747,068 A | 5/1998 | Mendizabal |
| 5,854,267 A | 12/1998 | Berlin et al. |
| 5,976,578 A | 11/1999 | Beyerle et al. |
| 6,149,943 A | 11/2000 | McTeigue et al. |
| 6,294,192 B1 | 9/2001 | Patel et al. |
| 6,455,518 B2 | 9/2002 | Zenke et al. |
| 6,544,556 B1 | 4/2003 | Chen et al. |
| 6,569,463 B2 | 5/2003 | Patel et al. |
| 6,613,354 B2 | 9/2003 | Depui et al. |
| 6,660,303 B2 | 12/2003 | Staniforth |
| 6,552,047 B2 | 4/2004 | Garvey et al. |
| 6,923,988 B2 | 8/2005 | Patel et al. |
| 6,926,907 B2 * | 8/2005 | Plachetka ............. 424/472 |
| 6,951,657 B1 | 10/2005 | Zuccarelli et al. |
| 7,169,809 B2 | 1/2007 | Berthelette et al. |
| 2003/0069255 A1 | 4/2003 | Plachetka et al. |
| 2003/0178031 A1 | 9/2003 | Du Pen et al. |
| 2004/0235802 A1 | 11/2004 | Gimona |
| 2005/0020671 A1 | 1/2005 | Fernandez Ibanez et al. |
| 2005/0053655 A1 | 3/2005 | Yang et al. |
| 2005/0163847 A1 | 7/2005 | Cheng et al. |
| 2005/0196459 A1 | 9/2005 | Castan et al. |
| 2005/0249806 A1 | 11/2005 | Proehl et al. |
| 2005/0249811 A1 | 11/2005 | Plachetka |
| 2006/0078614 A1 * | 4/2006 | Venkatesh ............. 424/469 |
| 2006/0127478 A1 * | 6/2006 | Zerbe et al. ............. 424/472 |
| 2006/0177504 A1 | 8/2006 | Sundharadas |
| 2007/0003490 A1 * | 1/2007 | Nijhawan ............. 424/48 |
| 2007/0043096 A1 | 2/2007 | Tidmarsh et al. |
| 2007/0043097 A1 | 2/2007 | Tidmarsh et al. |
| 2008/0020040 A1 | 1/2008 | Tidmarsh et al. |
| 2008/0021078 A1 * | 1/2008 | Tidmarsh et al. ............. 514/370 |
| 2008/0063706 A1 | 3/2008 | Tidmarsh et al. |

FOREIGN PATENT DOCUMENTS

| EP | 0 320 550 A1 | 6/1989 |
|---|---|---|
| EP | 0 321 613 A1 | 6/1989 |
| GB | 2 105 193 A | 3/1983 |
| WO | WO 91/16886 A1 | 11/1991 |
| WO | WO 94/07541 A1 | 4/1994 |
| WO | WO 02/22108 A1 | 3/2002 |
| WO | WO 02/066002 A2 | 8/2002 |
| WO | WO 02/098352 A2 | 12/2002 |
| WO | WO 2004/064815 A1 | 8/2004 |
| WO | WO 2007/012019 A2 | 1/2007 |
| WO | WO 2007/012022 A2 | 1/2007 |
| WO | WO 2008/011426 A2 | 1/2008 |
| WO | WO 2008/027963 A2 | 3/2008 |
| WO | WO 2010/009432 A1 | 1/2010 |

OTHER PUBLICATIONS

Aly, A. M.; Kittaneh, R. H. Formulation and Evaluation of Famotidine and Ibuprofen Chewable Tablets. J. J. Appl. Sci., 2004, vol. 6, No. 2, pp. 1-7.*

Notice of Allowance issued on Sep. 2, 2011 on U.S. Appl. No. 11/779,204.

Final Rejection issued on Aug. 12, 2011 on U.S. Appl. No. 11/489,275.

Advisory Action issued on Sep. 6, 2011 on U.S. Appl. No. 11/489,275.

Final rejection issued on Aug. 15, 2011 on U.S. Appl. No. 11/489,705.

Final rejection issued on Aug. 15, 2011 on U.S. Appl. No. 11/489,272.

Abraham et al., "National adherence to evidence-based guidelines for the prescription of nonsteroidal anti-inflammatory drugs," Gastroenterology 129:1171-1178 (2005).

Altman "Review of Ibuprofen for Osteoarthritis," Am. J. Med. 10:18 (1984).

(Continued)

*Primary Examiner* — Robert A Wax
*Assistant Examiner* — Jessica N. Worsham
(74) *Attorney, Agent, or Firm* — Foley & Lardner LLP

(57) ABSTRACT

Stable pharmaceutical compositions of famotidine and ibuprofen in a single unit dosage form are disclosed herein. The compositions comprise a famotidine core having a reduced or minimal surface area surrounded by a layer of ibuprofen. In some embodiments, the ibuprofen is in direct physical contact with the famotidine.

16 Claims, No Drawings

OTHER PUBLICATIONS

Aly et al., "Formulation and evaluation of famotidine and ibuprofen chewable tablets," Jordan Journal of Applied Sciences-Natural Sciences 6(2):1-7 (2004).

American College of Rheumatology Ad Hoc Group on Use of Selective and Nonselective Nonsteroidal Antiinflammatory Drugs "Recommendations for Use of Selective and Nonselective Nonsteroidal Antiinflammatory Drugs," Arthritis & Rheumatism 59(3):1058-1073 (2008).

American Hospital Formulary Service. Drug Information 88, p. 1659-1664 (1988).

American Society of Health-System Pharmacists, AHFS Drug Information 2006. McEvoy, ed., pp. 2902-2908 (2006).

Analysis of HZ-CA-004 Study Data, prepared Nov. 2007.

Bell et al., "Time to maximum effect of lansoprazole on gastric pH in normal male volunteers," Aliment. Pharmacal. Ther. 10(6):897-904 (1996).

Brady, W.M., M.D., et al., "Gastroesophageal reflux disease the long and the sort of therapeutic options", Postgraduate Medicine online, 100(5) (1996).

Castell, D.O., "Rationale for high-dose H2-receptor blockade in the treatment of gastro-oesophageal reflux disease", Ailment. Pharmacol. Therap., 1991,5 *Suppl. 1), 59-67.

Chambers et al., "A Cohort Study of NSAID Use and the Management of Related Gastrointestinal Symptoms by Primary Care Patients" P&T 27(7):462-467 (Jul. 2003).

Chremos et al, Clinical Pharmacology of Famotidine: a summary, (1987), J Clin Gastroenterolo, 9(Suppl 2):7-12.

Chremos et al, Pharmacodynamics of Famotidine in Humans, Am J Med, (1986), 81(Suppl 4B):24.

Cohen, "Dose Discrepancies Between the Physicians Desk Reference and the Medical Literature, and Their Possible Role in the High Incidence of Dose-Related Adverse Drug Events", Archive of Internal Medicine, Apr. 9, 2001, 161:957-964.

Copending U.S. Appl. No. 11/489,269, filed Jul. 18, 2006.
Copending U.S. Appl. No. 11/489,275, filed Jul. 18, 2006.
Copending U.S. Appl. No. 11/489,705, filed Jul. 18, 2006.
Copending U.S. Appl. No. 11/489,272, filed Jul. 18, 2006.

Davies "Clinical pharmacokinetics of ibuprofen. The first 30 years" Clin. Pharmacokinet. 34:101-154 (1998).

Davies et al, Ibuprofen: a review of its pharmacological properties, Drugs, (1971), 2:416-446.

De Klerk et al., Abstract of "Patient compliance in rheumatoid arthritis polymyalgia rheumatic, and gout" J. Rheumatol. 30(1):44-54 (Jan. 2003).

Dial et al., "Proton pump inhibitor use and risk of community-acquired Clostridium difficile-associated disease defined by prescription for oral vancomycin therapy," CMAJ 175(7):745-748 (Sep. 26, 2006).

Doherty et al., "Multiple Endocrine Neoplasias" Cancer: Principles and Practice of Oncology, 6th edition. J.B. Lippincott Co. pp. 1834-1839 (2001).

Drug Facts and Comparisions, 1997 Edition pp. 1387-1399, pp. 1933-1947.

DRUGS.COM, Famotidine Tablets, www.drugs.com/pro/famotindine, downloaded Jun. 7, 2007.

Duexis Label, 16 pages, Apr. 2011.

Echizen et al., "Clinical Pharmacokinetics of Famotidine," Clin. Pharmacokinet. 21(3):178-194 (1991).

Edge et al, High dose famotidine in ranitidine resistant severe oesophagitis: a pilot study, New Zealand Med J, (1990), 11:150-152.

Embase Abstract of Adel, et al., 2004, "Formulation and evaluation of famotidine and ibuprofen chewable tablets," Jordan Journal of Applied Sciences—Natural Sciences, vol. 6, No. 2, pp. 1-7.

European Supplementary Search Report and Search Opinion issued in Patent Application 06800140.3; Mail Date: Nov. 13, 2009, Completion Date: Nov. 2, 2009.

European Supplementary Search Report and Search Opinion issued in Patent Application 07813027.5; Mail Date: Oct. 27, 2009, Completion Date: Oct. 15, 2009.

FDA Drug Bulletin, vol. 19, No. 1, Feb. 1989.

FDA Facsimile dated May 16, 2006 regarding IND 72,116 HZT-501 (Ibuprofen and Famotidine) EOP2 Meeting.

Federal Register, vol. 75, No. 169, Wednesday, Sep. 1, 2010.

Gabriel et al., "Risk for serious gastrointestinal complications related to use of nonsteroidal anti-inflammatory drugs. A meta-analysis," Ann. Intern. Med. 115(10):787-796 (1991).

Garcia et al., "Gastrointestinal Prophylactic Therapy Among Patients with Arthritis Treated by Rheumatology Specialists" *J. Rheumatol.* (Mar. 1, 2006) vol. 33 (No. 4): 779-784.

Geis et al., "Prevalence of Mucosal Lesions in the Stomach and Duodenum Due to Chronic Use of NSAID in Patients with Rheumatoid Arthritis or Osteoarthritis, and Interim Report on Prevention by Misoprostol of Diclofenac Associated Lesions," J. Rheumatol. 18(suppl 28):11-14 (1991).

Gillin et al., "Problems related to acid rebound and tachyphylaxis" Best Practice & Research Clinical Gastroenterology 15(3):487-495 (2001).

Ho et al., "Risk of Adverse Outcomes Associated with concomitant use of clopidogrel and proton pump inhibitors follong acute coronary syndrome" JAMA 301(9):937-944 (Mar. 4, 2009).

Horizon Therapeutics "Horizon Therapeutics" PowerPoint Presentation, May 12, 2009.

Horizon Therapeutics: "PIND 72,116 / ibuprofen/famotidine combo product Pre-IND Meeting," (Jun. 13, 2005).

Howden et al., "The Tolerability and Safety of Famotidine" Clinical Therapeutics 18(1):36-54 (1996).

Hudson et al., "Famotidine for Healing and Maintenance in Nonsteroidal anti-inflammatory Drug-Associated Gastroduodenal Ulceration," Gastroenterology 112:1817-1822 (1997).

HZT-501 Follow-on Safety Study (HZ-CA-304), (2009).

HZT-501 Phase 3 Trials: Reduce-1 and Reduce-2, 2009.

Inpharma (1994) Symposia: Minimising the GI risks of NSAIDs. ISSN 1173-8324.

International Search Report and Written Opinion for PCT/US06/28078 dated Aug. 3, 2007.

International Search Report and Written Opinion for PCT/US06/28078 dated May 23, 2007.

International Search Report and Written Opinion for PCT/US07/73716 dated Sep. 24, 2008.

Johnson, D., "Medical Therapy for Gastroesophageal Reflux Disease," Amer. J. Med., May 27, 1992, vol. 92 (suppl. 5A), pp. 5A-88S-5A-97S.

Kantor, T.G., "Ibuprofen" Ann. of Int. Med. 91:1877-1882 (1979).

Koch et al., "Prevention of Nonsteroidal Anti-inflammatory Drug-Induced Gastrointestinal Mucosal Injury," Arch. Intern. Med. 156:2321-2332 (1996).

Krishna et al., "Newer H2-Receptor Antagonists: Clinical Pharmacokinetics and Drug Interaction Potential" Clinical Pharmacokinetics 15:205-215 (1988).

Lanza et al., "Guidelines for Prevention of NSAID-Related Ulcer Complications" Am. J. Gastroenterol. 104:728-738 (2009).

Larkai et al., "Dyspepsia in NSAID users: the size of the problem" J. Clin. Gastroenterol. 11(2):158-162 (1989).

Lin "Pharmacokinetic and pharmacodynamic properties of histamine H2-receptor antagonists. Relationship between intrinsic potency and effective plasma concentrations" Clin. Pharmacokinet. 20:218-236 (1991).

Loren et al., "Physicians Fail to Provide Protective Co-Therapy for High GI Risk Patients Taking NSAIDs—Even with Direct Interactive Communication and Free PPI: Results of a Prospective Outcomes Trial," Abstract DDW 2008.

Merki et al., "Double blind comparison of the effects of cimetidine, ranitidine, famotidine, and placebo on intragastric acidity in 30 normal volunteers" Gut 29:81-84 (1988).

Nwokolo et al., "Tolerance during 29 days of conventional dosing with cimetidine, nizatidine, famotidine or ranitidine" Aliment. Pharmacal. Ther. 4(suppl. 1):29-45 (1990).

Opadry® II Brochure, 1990.

PDR 53rd Edition, pp. 1856-1859 (1999).

Pelletier et al., "Efficacy & Safety of Diacerein in Osteoarthritis of the Knee" Arthritis & Rheumatism 43(10):2339-2348 (2000).

Pepcid (famotidine) tablet, film coated [Merck & Co., Inc.], retrieved Mar. 14, 2009 from http://dailymed.nlm.nih.gov/dailymed/drugInfo.cfm?id=8919.

Pifferi et al., "Quality and functionality of excipients" Farmaco 54(1-2):1-14 (2005).

Plachetka et al., "Integrated Gastric Acidity Can Predict the Prevention of Naproxen-Induced Gastroduodenal Pathology in Normal Subjects," American Gastroenterological Association Meeting (2003).

Porro et al, Famotidine in the treatment of gastric and duodenal ulceration, Karger Intl J Gastroenter Digestion, (1985), 32(Suppl 1):62-69.

Pre-IND Meeting Background Information: "Fixed Dose Combination Product of ibuprofen and famotidine for Pain Relief," May 9, 2005.

Protocol: "Double Blind Follow on Safety Study of HZT-501 in Subjects Who Have Completed Participation in Horizon Protocol HZ-CA-301 or Horizon Protocol HZ-CA-303," Feb. 28, 2007.

U.S. Appl. No. 60/700,481, filed Jul. 18, 2005.

Rammer et al., "Prophylaxe NSAR-induzierter Ulzera" Journal für Gastroenterologische und Hepatologische Erkrankungen [online] 2(4) (2004). Retrieved from the Internet: http://www.kup.at/kup/pdf/4820.pdf [retrieved on Oct. 30, 2009].

Remington's Pharmaceutical Sciences, 18th Edition, p. 726-738 (1990).

Richy et al. "Time dependent risk of gastrointestinal complications induced by non-steroidal anti-inflammatory drug use: a consensus statement using a meta-analytic approach" Ann. Rheum. Dis. 63:759-766 (2004).

Rodriguez et al., "Risk of upper gastrointestinal bleeding and perforation associated with individual non-steroidal anti-inflammatory drugs" Lancet 343(8900):769-72 (1994).

Rostom et al., "Prevention of NSAID-induced gastrointestinal ulcers" Cochrane Database Syst. Rev. 4:CD002296 (2002).

Roumie et al., "Nonaspirin NSAIDs, Cyclooxygenase 2 Inhibitors, and the Risk for Stroke," Stroke (39):2037-2045 (2008).

Santana et al, Effect of oral famotidine on 24 hour intragastric acidity, Postgrad Med J (UK), (1986), 62(Supp 2):39-42.

Scheiman, "Nonsteroidal Anti-Inflammatory Drugs, Aspirin, and Gastrointestinal Prophylaxis: An Ounce of Prevention" Reviews in Gastroenterological Disorders 5(2):S39-S49 (2005).

Schnitzer et al., "Use of nonsteroidal anti-inflammatory drugs and gastroprotective agents before the advent of cyclooxygenase-2-selective inhibitors: analysis of a large United States claims database." Clinical Therapeutics 2001 vol. 23 No. 12 1984-1998.

ScienceDaily, "Proton Pump Inhibitors Increase Risk of Heart Attacks for Patients on Common Cardiac Drug, Study Shows," Jan. 30, 2009.

Silverstein et al., "Misoprostol reduces serious gastrointestinal complications in patients with rheumatoid arthritis receiving anti-inflammatory drugs. A randomized, double-blind, placebo-controlled trial" Ann. Intern. Med. 123(4):241-249 (1995).

Simon et al., "A Dose-Ranging Study of Famotidine in Prevention of Gastroduodenal Lesions Associated with Nonsteroidal Anti-inflammatory Drugs (NSAIDS): Results of a U.S. Multicenter Trial" Abstracts Submitted for 59th Annual Scientific Meeting American College of Gastroenterology. Am. J. Gastroenterol. 89(9):1644 (1994).

Singh et al., "Gastrointestinal tract complications of nonsteroidal anti-inflammatory drug treatment in rheumatoid arthritis. A prospective observational cohort study" Arch. Intern. Med. 156(14):1530-1536 (1996).

Singh et al., "NSAID Induced Gastrointestinal Complications: The ARAMIS Perspective—1997" J. Rheumatol. 25(suppl 51):8-16 (1998).

Singh et al., "Decreased Use of Cox-2 Inhibitors Is Increasing Gastrointestinal Complications," American College of Rheumatology (ACR), (Oct. 30, 2007).

Singh, G. "Recent Considerations in Non-Steroidal Anti-Inflammatory Gastropathy" Am. J. Med. 105(1B):31S-38S (1998).

Smith et al, Clinical pharmacology of famotidine, Karger Intl J Gastroenter Digestion, (1985), 32(Suppl 1):15-23.

Sørensen et al. "Risk of upper gastrointestinal bleeding associated with use of low-dose aspirin" Am. J. Gastroenterol. 995(9):2218-2224 (2000).

Sturkenboom et al., "Adherence to proton pump inhibitors or H2-receptor antagonists during the use of non-steroidal anti-inflammatory drugs" Aliment Pharmacol. Ther., 18(11-12):1137-1147 (2003).

Suzuki et al. "Four-day continuous gastric pH monitoring following anti-acid secretory drug administration: cross-over test to assess the early effects" Aliment Pharmacol. Ther., 27(1):66-71 (2007).

Swift et al., "Effect of Ranitidine on Gastroduodenal Mucosal Damage in Patients on Long Term Non Steroidal Anti-inflammatory Drugs," Digestion 44:86-94 (1989).

Taha et al, Famotidine for the prevention of gastric and duodenal ulcers caused by nonsteroidal antiinflammatory drugs, N Engl J Med, (1996), 334:1435-1439.

Tamura et al. "Effects of Diacerein on Indomethacin-Induced Gastric Ulceration" Pharmacology 63:228-233 (2001).

Targownik et al., "Use of proton pump inhibitors and risk of osteoporosis-related fractures," CMAJ, 179(4):319-326 (Aug. 12, 2008).

Thiefin et al., "Characteristics and Impact of Upper GI Symptoms in Patients Treated with NSAIDs: Results of a Cross Sectional Epidemiological Study in Primary Care," Abstract DDW Presentation, (May 2008).

U.S. Appl. No. 11/489,272—Non-final Office Action (Restriction Requirement) dated Dec. 16, 2009.

U.S. Appl. No. 11/489,272—Non-final Office Action dated Oct. 14, 2010.

U.S. Appl. No. 11/489,275—Non-final Office Action (Restriction Requirement) dated Dec. 31, 2009.

U.S. Appl. No. 11/489,275—Non-final Office Action (Restriction Requirement) dated Sep. 10, 2010.

U.S. Appl. No. 11/489,705—Non-final Office Action (Restriction Requirement) dated Dec. 31, 2009.

U.S. Appl. No. 11/489,705—Non-final Office Action dated Oct. 1, 2010.

U.S. Appl. No. 11/489,269, filed Jul. 18, 2006: Prosecution History through Jun. 15, 2010.

U.S. Appl. No. 11/779,204—Non-final Office Action (Restriction Requirement) dated Jun. 10, 2010.

U.S. Appl. No. 11/779,204—Non-final Office Action dated Mar. 16, 2011.

U.S. Appl. No. 11/489,275—Non-final Office Action dated Jan. 19, 2011.

Valenti, "Expanding role of coformulations in the treatment of HIV infection: impact of fixed dose combinations," Antiretroviral Therapy (Dec. 21, 2004).

Vinayek et al, Famotidine in the therapy of gastric hypersecretory states, Am J Med, (1986), 81(S4B):49-59.

Ward, "Update on Ibuprofen for Rheumatoid Arthritis," Am. J. Med. 77(1A): 39 (1984).

Welage, "Overview of pharmacologic agents for acid suppression in critically ill patients", America Journal of Health-System Pharmacy, May 15, 2005, vol. 62, No. 10, Suppl. 2, pp. S4-S11.

Wolfe et al., "Gastrointestinal Toxicity of Nonsteroidal Antiinflammatory Drugs," N.E. J. Med. 340(24):1888-1899 (1999).

Wu et al., "Does famotidine have similar efficacy to misoprostol in the treatment of non-steroidal anti-inflammatory drug-induced gastropathy?" IJCP 52(7):472-474 (Oct. 1998).

Yang et al., "Long term proton pump inhibitor therapy and risk of hip fracture," JAMA, vol. 296 No. 24:2947-2953 (Dec. 27, 2006).

Yazdanian et al., "The 'High Solubility' Definition of the Current FDA Guideline on Biopharmaceutical Classification System May Be Too Strict for Acidic Drugs," Pharmaceutical Res. 21(2):293-299 (2004).

Zeleznik et al., "High Functionality Excipients (HFE)—PROSOL® SMCC as an Effective Strategy for Generic Drug Formulation," Business Briefing: Pharmagenerics (2004).

* cited by examiner

US 8,067,033 B2

STABLE COMPOSITIONS OF FAMOTIDINE AND IBUPROFEN

CROSS-REFERENCE TO RELATED APPLICATIONS

This application claims the benefit under 35 U.S.C. 119(e) of U.S. Provisional Patent Application No. 60/991,628, filed Nov. 30, 2007, which is incorporated herein by reference in its entirety for all purposes.

FIELD OF THE INVENTION

This invention relates to pharmaceutical compositions containing ibuprofen and famotidine, and finds application in the field of medicine.

BACKGROUND OF THE INVENTION

Ibuprofen, a non-steroidal anti-inflammatory drug (NSAID), has been used in humans for nearly forty years. While generally regarded as safe, ibuprofen and other NSAIDs can cause gastritis, dyspepsia, and gastric and duodenal ulceration. Gastric and duodenal ulceration is a consequence of impaired mucosal integrity resulting from ibuprofen-mediated inhibition of prostaglandin synthesis. This side-effect is a particular problem for individuals who take ibuprofen for extended periods of time, such as patients suffering from rheumatoid arthritis and osteoarthritis.

The risk of developing gastric or duodenal ulceration can be reduced by cotherapy with the drug famotidine. Famotidine blocks the action of the histamine type 2 (H2) receptor, leading to a reduction of acid secretion in the stomach. Reducing stomach acid with famotidine during treatment with certain nonsteroidal anti-inflammatory drugs is reported to decrease incidence of gastrointestinal ulcers (see Taha et al., 1996, "Famotidine for the prevention of gastric and duodenal ulcers caused by nonsteroidal anti-inflammatory drugs" *N Engl J Med* 334:1435-9, and Rostom et al., 2002, "Prevention of NSAID-induced gastrointestinal ulcers" *Cochrane Database Syst Rev* 4:CD002296).

Although NSAID plus famotidine cotherapy reduces risk of developing gastric or duodenal ulceration, such therapies are not widely used. One explanation for this observation is that patient compliance is more problematic with a regimen that requires administration of two separate dosage forms. Efforts to develop a single unit dosage form comprising both ibuprofen and famotidine have been successful (see co-pending U.S. application Ser. Nos. 11/489,275, filed Jul. 18, 2006, 11/489,705, filed Jul. 18, 2006, and 11/779,204, filed Jul. 17, 2007), but were made more challenging by the discovery that ibuprofen and famotidine are chemically incompatible. Moreover, those dosage forms that have been described could be improved with respect to stability under "forced degradation" or "accelerated" conditions of elevated temperature and humidity. Forced degradation conditions are intended to accelerate the process of chemical degradation for a period of time and are used to predict the effect of storage under more benign conditions (e.g., room temperature) for a longer period of time.

There remains a need for new and improved unit dosage forms comprising ibuprofen and famotidine that exhibit exceptional stability under forced degradation conditions. The present invention meets that need.

SUMMARY OF THE INVENTION

In one aspect, the present invention is directed to a pharmaceutical composition, comprising (i) a core comprising a therapeutically effective amount of famotidine, and (ii) a surrounding portion comprising a therapeutically effective amount of ibuprofen in direct physical contact with the core, wherein the famotidine and the ibuprofen are in direct physical contact over a surface area that does not exceed an area calculated from the formula: $(25\ mm^2)+(3.75\ mm^2 \cdot x)$, where x is the quantity (mg) of famotidine in the core, and wherein the composition is stable for at least 1 month at 40° C. and 75% relative humidity.

In some cases, the core comprises famotidine in an amount from 24 mg to 28 mg, and the shell comprises ibuprofen in an amount from 750 mg to 850 mg. In other cases, the core comprises about 26.6 mg of famotidine. In some embodiments, the core comprises famotidine in an amount from 24 mg to 28 mg, and the shell comprises ibuprofen in an amount from 575 mg to 625 mg. In some embodiments, the core comprises famotidine in an amount from 12 mg to 14 mg, and the shell comprises ibuprofen in an amount from 375 mg to 425 mg. In at least one embodiment, the ibuprofen is in the form of Ibuprofen DC 85™.

In some embodiments, the surface area of direct physical contact between the famotidine and the ibuprofen does not exceed 120 $mm^2$. In some embodiments, the surface area of direct physical contact between the famotidine and the ibuprofen does not exceed 100 $mm^2$. In at least one embodiment, the surface area of direct physical contact between the famotidine and the ibuprofen does not exceed 65 $mm^2$.

In some embodiments, the core is substantially spherical in shape. In other embodiments, the core is substantially cylindrical in shape.

In another aspect, the present invention is directed to a pharmaceutical composition, comprising (i) a core comprising from 24 mg to 28 mg of famotidine, and (ii) a surrounding portion comprising from 775 mg to 825 mg of ibuprofen in direct physical contact with the core, wherein the famotidine and the ibuprofen are in direct physical contact over a surface area that does not exceed 130 $mm^2$, and wherein the composition is stable for at least 1 month at 40° C. and 75% relative humidity.

In at least one embodiment, the ibuprofen is in the form of Ibuprofen DC 85™.

In some embodiments, the core is substantially cylindrical in shape and the surface area of direct physical contact between the famotidine and the ibuprofen does not exceed 120 $mm^2$. In some embodiments, the surface area of direct physical contact between the famotidine and the ibuprofen does not exceed 115 $mm^2$. In some embodiments, the core is substantially spherical in shape and the surface area of direct physical contact between the famotidine and the ibuprofen does not exceed 100 $mm^2$.

DETAILED DESCRIPTION

I. Definitions

"Famotidine" refers to 3-[2-(diaminomethyleneamino) thiazol-4-ylmethylthio]-N-sulfamoylpropionamidine, including the polymorphic forms designated Form A and Form B (see, e.g. U.S. Pat. Nos. 5,128,477 and 5,120,850) and their mixtures, as well as pharmaceutically acceptable salts thereof. Famotidine can be prepared using art-known methods, such as the method described in U.S. Pat. No. 4,283,408. Famotidine's properties have been described in the medical literature (see, e.g., Echizen et al., 1991, *Clin Pharmacokinet.* 21:178-94).

"Ibuprofen" refers to 2-(p-isobutylphenyl) propionic acid ($C_{13}H_{18}O_2$), including various crystal forms and pharmaceutically acceptable salts. Two enantiomers of ibuprofen exist. As used herein in the context of solid formulations of the invention, "ibuprofen" refers to a racemic mixture or both enantiomers as well as racemic mixtures that contain more of one enantiomer than another (including, for example, mixtures enriched in the S-enantiomer), and enantiomerically pure preparations (including, for example, compositions substantially free of the R-enantiomer). Ibuprofen is available commercially, typically as a racemic mixture, and, for example, ibuprofen preparations with mean particle sizes of 25, 38, 50, or 90 microns can be obtained from BASF Aktiengesellschaft (Ludwigshafen, Germany). One useful ibuprofen product is a directly compressible formulation described in WO 2007/042445 (incorporated herein by reference), a version of which is available from BASF under the trade name Ibuprofen DC 85™. Ibuprofen's properties have been described in the medical literature (see, e.g., Davies, 1998, "Clinical pharmacokinetics of ibuprofen. The first 30 years" *Clin Pharmacokinet* 34:101-54).

A "therapeutically effective amount" of ibuprofen is an amount of ibuprofen or its pharmaceutically acceptable salt which eliminates, alleviates, or provides relief of the symptoms for which it is administered.

A "therapeutically effective amount" of famotidine is an amount of famotidine or its pharmaceutically acceptable salt which suppresses gastric acid secretion, or otherwise eliminates, alleviates, or provides relief of the symptoms for which it is administered.

An "excipient," as used herein, is any component of an oral dosage form that is not an active pharmaceutical ingredient (i.e., ibuprofen and/or famotidine). Excipients include binders, lubricants, diluents, disintegrants, coatings, barrier layer components, glidants, and other components. Excipients are known in the art (see HANDBOOK OF PHARMACEUTICAL EXCIPIENTS, FIFTH EDITION, 2005, edited by Rowe et al., McGraw Hill). Some excipients serve multiple functions or are so-called high functionality excipients. For example, talc may act as a lubricant, and an anti-adherent, and a glidant. See Pifferi et al., 2005, "Quality and functionality of excipients" *Farmaco.* 54:1-14; and Zeleznik and Renak, *Business Briefing: Phar-magenerics* 2004.

As used herein, a "pharmaceutically acceptable" component is one that is suitable for use with humans and/or animals without undue adverse side effects (such as toxicity, irritation, and allergic response) commensurate with a reasonable benefit/risk ratio.

A "compartment" in the context of a unit dosage form is a physical region of a tablet or other dosage form. Two components of a unit dosage form are distinct compartments if there exists a recognizable demarcation between the two components, even though they may be in direct physical contact with one another.

The term "core," as used herein, refers to a single interior compartment of a unit dosage form comprising famotidine.

The term "shell," as used herein, refers to an exterior compartment of a unit dosage form comprising ibuprofen, which completely surrounds the core or famotidine compartment. As described herein, this exterior compartment may be overcoated for cosmetic or other reasons, in particular embodiments.

The term "direct physical contact" refers to the absence of a barrier layer between components or adjacent compartments of a unit dosage form.

The term "stable," as used herein, refers to a composition in which the active pharmaceutical ingredients (i.e., ibuprofen and famotidine) are present in an amount of at least 90%, and preferably at least 95%, at least 96%, at least 97%, at least 98%, at least 99%, or at least 99.5% of the originally specified amount for each such ingredient, and no more than 3%, and preferably no more than 2%, no more than 1%, no more than 0.9%, no more than 0.8%, no more than 0.7%, or no more than 0.6% sulfamide is present after a specified period of time and under specified conditions.

The term "about," as used herein, is intended to indicate a range (e.g., ±10%) caused by experimental uncertainty, variations resulting from manufacturing tolerances, or variations within the parameters of a label claim associated with a drug product.

The term "substantially," as used herein with reference to the spherical or cylindrical shape of the core of a pharmaceutical composition or unit dosage form refers to variability resulting from manufacturing tolerances, as well as intentional deviations from these precise geometric shapes. For example, in a sphere the three axes are of identical length. In this context, the term "substantially" is intended to indicate a tolerance for a deviation of ±5% in the length of one or two of the axes in relation to the third axis, thus encompassing an oblongation or other variation of a spherical shape. In the context of a cylinder, the term "substantially" is intended to indicate a tolerance for a deviation of +5% in the diameter of the cylinder along its length. For example, if the diameter increases from either end of the "cylinder" to a central position, the shape may be more appropriately referred to as a "barrel," but is still intended to be encompassed by the phrase "substantially cylindrical in shape."

II. Tablet-in-Tablet Compositions

Pharmaceutical compositions in accordance with the present invention comprise ibuprofen and famotidine in a single unit dosage form. In one aspect, the present invention relates to an oral dosage form comprising ibuprofen and famotidine, and optionally, one or more pharmaceutically acceptable excipients. It has been discovered that by reducing the surface area of direct physical contact between ibuprofen and famotidine, one can attain an unexpectedly profound increase in stability relative to alternative designs (e.g., barrier-coated famotidine multiparticulates in a matrix comprising ibuprofen). Moreover, using the design of the present invention, the barrier layer can be omitted without sacrificing stability.

In one embodiment of the present invention, the pharmaceutical composition comprises a core comprising a therapeutically effective amount of famotidine, and a surrounding portion comprising a therapeutically effective amount of ibuprofen in direct physical contact with the core, e.g., a tablet-in-tablet formulation. The surface area over which the famotidine and ibuprofen are in direct physical contact is controlled so as not to exceed an area calculated from the following formula (Formula (I)):

$$(25 \text{ mm}^2) + (3.75 \text{ mm}^2 \cdot x),$$

where x is the quantity, in milligrams, of famotidine in the core. This pharmaceutical formulation provides a composition which is stable for at least one month at 40° C. and 75% relative humidity.

In other embodiments, the surface area of the famotidine core is as described above with reference to Formula (I), but rather than being in direct physical contact with the ibuprofen shell, a barrier layer is interposed between the two compartments. Generally, the barrier layer may comprise a water-soluble, pH independent film that promotes immediate disintegration for rapid release of the famotidine core. Materials that can be used for readily soluble films are well known in the art and include cellulose derivatives such as hydroxypropylmethyl cellulose, hydroxypropyl cellulose, hydroxypropyl methylcellulose phthalate, cellulose acetate phthalate, and ethyl cellulose; methacrylic polymers, amino-alkylmethacrylate copolymers (e.g. Eudragit™E), polyvinyl acetate phthalate and polyvinyl alcohol (PVA). A plasticizer (e.g., triacetin, diethyl phthalate, tributyl sebacate or polyethylene glycol) may also be included. The barrier layer may include an antiadherent or glidant (e.g., talc, fumed silica or magnesium stearate) and colorants such as titanium dioxide, iron oxide based colorants or others. In one embodiment the barrier layer comprises a non-toxic edible polymer, edible pigment particles, an edible polymer plasticizer, and a surfactant. Materials include, for example and not limitation, materials described in U.S. Pat. No. 4,543,370 (Colorcon), incorporated herein by reference. Exemplary barrier layers include OPADRY®, which is available from Colorcon (West Point Pa. USA); OPADRY II® which is available from Colorcon (West Point Pa. USA) and comprises HPMC, titanium dioxide, plasticizer and other components; and polyvinyl alcohol-polyethylene glycol copolymer marketed as Kollicoat® IR (BASF). Suitable barrier layers, for illustration and not limitation, include Kollicoat® IR (a polyvinyl alcohol-polyethylene glycol graft copolymer) and Kollicoat IR White® both manufactured by BASF Aktiengesellschaft (Ludwigshafen, Germany). The thickness of the barrier layer can vary over a wide range, but is generally in the range 20 to 3,000 microns, such as on the order of about 25 to 250 microns. Preferably the barrier layer retards the release of famotidine by less than 5 minutes, preferably less than 4 minutes and more preferably by less than 3 minutes.

A. Famotidine Compartment

Pharmaceutical compositions in accordance with the present invention comprise a famotidine compartment structured as a core comprising a therapeutically effective amount of famotidine. The core can include both famotidine and, optionally, one or more pharmaceutically acceptable excipients.

The core can include an amount of famotidine suitable, for example, for the methods of treatment described hereinafter. For example, the core can comprise from 24 mg to 28 mg of famotidine, from 12 mg to 14 mg of famotidine, or the like, in various formulations consistent with the present invention. In some embodiments, the famotidine compartment comprises a core comprising about 13.3 mg or about 26.6 mg of famotidine.

B. Ibuprofen Compartment

Pharmaceutical compositions of the present invention further comprise an ibuprofen compartment comprising a therapeutically effective amount of ibuprofen surrounding and, in some embodiments, in direct physical contact with the famotidine core described above. The surrounding portion of ibuprofen is, in some embodiments, in direct physical contact with the core over a surface area defined by the dimensions of the core, which does not exceed an area calculated from Formula (I).

The ibuprofen compartment can include an amount of ibuprofen suitable, for example, for the methods of treatment described hereinafter, and, optionally, one or more pharmaceutically acceptable excipients. For example, the ibuprofen shell can comprise from 750 mg to 850 mg of ibuprofen, from 575 mg to 625 mg of ibuprofen, from 375 mg to 425 mg of ibuprofen, or the like, in various formulations consistent with the present invention. In some embodiments, the ibuprofen compartment comprises a surrounding portion comprising from 775 mg to 825 mg of ibuprofen, or, in one embodiment, 800 mg of ibuprofen. In other embodiments, the compositions and/or unit dosage forms of the present invention comprise ibuprofen and famotidine in a ratio of from about 29:1 to about 31:1, and preferably in a ratio of about 30:1. In some embodiments, the ibuprofen is in the form of Ibuprofen DC 85™.

C. Surface Area of Direct Physical Contact

The reduction, and in some embodiments, minimization, of the surface area of the core, or of direct physical contact between the active pharmaceutical ingredients, provides unexpected advantages in the formulation of stable pharmaceutical compositions of famotidine and ibuprofen. The reduction and/or minimization of the surface area of the core, or of direct physical contact between the incompatible active pharmaceutical ingredients, is achieved through control of the geometry of the famotidine compartment of unit dosage forms in accordance with the present invention.

As will be appreciated, a given amount of material (e.g., famotidine plus one or more excipients) occupies a specific volume defined by the density of the material. In the case of pharmaceutical compositions of the present invention, the density of the material will, in part, be determined by the pressure applied to compress the material into the famotidine compartment (i.e., the core), and more specifically by the dimensions of the equipment used in the manufacturing process. Tablet manufacturing techniques known in the art for other materials can be employed to prepare the famotidine compartment with the geometry being defined by the shape of the punches used to compress the material (i.e., famotidine plus one or more optional excipients).

The surface area of the core and the corresponding surface area of direct physical contact can be limited or, in some cases, minimized, by selecting a core geometry that can contain the desired quantity of famotidine and optional excipients in a volume that has a corresponding surface area that meets the criteria described above with reference to Formula (I). Although the addition of excipients increases the volume and the corresponding surface area of the famotidine core, the excipients may by useful, as described in greater detail hereinafter, to impart particular qualities to the famotidine component of the pharmaceutical composition, or to provide a beneficial characteristic that may be desirable for further processing to prepare the tablet-in-tablet formulation. In some embodiments, the famotidine component has a geometry that is substantially cylindrical in shape. In other embodiments, the famotidine component has a geometry that is substantially spherical in shape.

Without intending to limit the scope of the present invention, the following examples of surface area calculations are provided to illustrate this particular feature of the claimed invention. In an embodiment of the invention in which the famotidine compartment or core comprises about 26.6 mg of famotidine, the famotidine and the surrounding portion of ibuprofen are in direct physical contact over a surface area that does not exceed an area calculated from Formula (I), i.e., 25 mm$^2$+3.75 mm$^2$·26.6=124.75 mm$^2$. Similarly, a famotidine compartment comprising about 13.3 mg of famotidine will have an area of direct physical contact not to exceed 74.88 mm$^2$; i.e., 25 mm$^2$+3.75 mm$^2$·13.3=74.88 mm$^2$.

In other embodiments, the selection of geometry can further limit the surface area of direct physical contact between the famotidine core and the surrounding portion of ibuprofen. For example, if the core is substantially cylindrical in shape, and the radius of the cylinder approximates the length, about 26.6 mg of famotidine can be contained in a volume whose surface area does not exceed 120 mm$^2$, 119 mm$^2$, 118 mm$^2$, 117 mm$^2$, 116 mm$^2$, 115 mm$^2$, 114 mm$^2$, 113 mm$^2$, 112 mm$^2$, 111 mm$^2$, or 110 mm$^2$. In still other embodiments, the selection of geometry can be used to minimize the surface area of direct physical contact between the famotidine core and the surrounding portion of ibuprofen. In these cases, the core is substantially spherical in shape and can comprise about 26.6 mg of famotidine, for example, in a volume whose surface area does not exceed 100 mm², 99 mm², 98 mm², 97 mm², 96 mm², 95 mm², 94 mm², 93 mm², 92 mm², 91 mm², or 90 mm².

Various exemplary, non-limiting embodiments of the famotidine core in accordance with the present invention are provided in Table 1.

TABLE 1

Famotidine Core: Dimensions, Volume and Surface Area

| Shape | Radius | Length | Volume | Surface Area | Quantity* |
|---|---|---|---|---|---|
| Spherical | 2.73 mm | — | 84.78 mm³ | 93.33 mm² | 26.6 mg |
| Cylindrical | 3.00 mm | 3.00 mm | 84.78 mm³ | 113.04 mm² | 26.6 mg |
| Spherical | 2.79 mm | — | 90.43 mm³ | 97.42 mm² | 26.6 mg |
| Cylindrical | 3.00 mm | 3.20 mm | 90.43 mm³ | 116.81 mm² | 26.6 mg |
| Spherical | 2.70 mm | — | 81.98 mm³ | 91.22 mm² | 26.6 mg |
| Cylindrical | 2.95 mm | 3.00 mm | 81.98 mm³ | 110.23 mm² | 26.6 mg |
| Spherical | 2.17 mm | — | 42.5 mm³ | 58.87 mm² | 13.3 mg |
| Cylindrical | 2.39 mm | 2.39 mm | 42.5 mm³ | 71.44 mm² | 13.3 mg |
| Spherical | 1.72 mm | — | 21.25 mm³ | 37.11 mm² | 6.65 mg |
| Cylindrical | 1.89 mm | 1.89 mm | 21.25 mm³ | 44.96 mm² | 6.65 mg |

*Quantity of famotidine; core also includes excipients as identified in Example 1 in relative proportion.

As will be appreciated, a core having a particular volume defined by its dimensions will have an upper limit in regard to the quantity of excipients that can be included with a desired quantity of famotidine. In various embodiments, the ratio of famotidine to excipients in the core does not exceed from about 1:1.89 to about 1:2.36, from about 1:1.89 to about 1:2.84, from about 1:1.89 to about 1:3.31, or from about 1:1.89 to about 1:3.78. The excipients can include any one or more of the excipients identified in Example 1 herein, or other excipients known to those of skill in the art that are suitable for the specific application of the present invention.

D. Excipients

A variety of excipients may be combined with famotidine and/or ibuprofen in their respective compartments of the pharmaceutical compositions of the present invention. As mentioned above, the provision of various excipients may be useful to impart particular qualities to either the famotidine component or the ibuprofen component of the pharmaceutical composition, or to provide a beneficial characteristic that may be desirable for processing to prepare the tablet-in-tablet formulation. Pharmaceutically acceptable excipients useful in compositions of the present invention can include binders, lubricants, diluents, disintegrants, and glidants, or the like, as known in the art. See e.g., HANDBOOK OF PHARMACEUTICAL MANUFACTURING FORMULATIONS, 2004, Ed. Sarfaraz K Niazi, CRC Press; HANDBOOK OF PHARMACEUTICAL ADDITIVES, SECOND EDITION, 2002, compiled by Michael and Irene Ash, Synapse Books; and REMINGTON SCIENCE AND PRACTICE OF PHARMACY, 2005, David B. Troy (Editor), Lippincott Williams & Wilkins.

Binders useful in compositions of the present invention are those excipients that impart cohesive qualities to components of a pharmaceutical composition. Commonly used binders include, for example, starch; sugars, such as sucrose, glucose, dextrose, and lactose; cellulose derivatives such as powdered cellulose, microcrystalline cellulose, silicified microcrystalline cellulose (SMCC), hydroxypropylcellulose, low-substituted hydroxypropylcellulose, hypromellose (hydroxypropylmethylcellulose); and mixtures of these and similar ingredients.

Lubricants can be added to components of the present compositions to reduce sticking by a solid formulation to the equipment used for production of a unit does form, such as, for example, the punches of a tablet press. Examples of lubricants include magnesium stearate and calcium stearate. Other lubricants include, but are not limited to, aluminum-stearate, talc, sodium benzoate, glyceryl mono fatty acid (e.g., glyceryl monostearate from Danisco, UK), glyceryl dibehenate (e.g., CompritolATO888™ Gattefosse France), glyceryl palmitostearic ester (e.g., Precirol™, Gattefosse France), polyoxyethylene glycol (PEG, BASF) such as PEG 4000-8000, hydrogenated cotton seed oil or castor seed oil (Cutina H R, Henkel) and others.

Diluents can be added to components of a pharmaceutical composition to increase bulk weight of the material to be formulated, e.g. tabletted, in order to achieve the desired weight.

Disintegrants useful in the present compositions are those excipients included in a pharmaceutical composition in order to ensure that the composition has an acceptable disintegration rate in an environment of use. Examples of disintegrants include starch derivatives (e.g., sodium carboxymethyl starch and pregelatinized corn starch such as starch 1500 from Colorcon) and salts of carboxymethylcellulose (e.g., sodium carboxymethylcellulose), crospovidone (cross-linked PVP polyvinylpyrrolidinone (PVP), e.g., Polyplasdone™ from ISP or Kollidon™ from BASF).

Glidants refer to excipients included in a pharmaceutical composition to keep the component powder flowing as a tablet is being made, preventing formation of lumps. Nonlimiting examples of glidants are colloidal silicon dioxides such as CAB-O-SIL™ (Cabot Corp.), SYLOID™, (W.R. Grace & Co.), AEROSIL™ (Degussa), talc, and corn starch.

E. Stability of Tablet-in-Tablet Compositions

Tablet-in-tablet compositions of the present invention comprising a famotidine compartment and an ibuprofen compartment surrounding and, in some embodiments, in direct physical contact with the famotidine compartment are stable for extended periods under "forced degradation" conditions of elevated temperature and relative humidity. For example, compositions of famotidine and ibuprofen prepared as described in the "Examples" section, hereinbelow, exhibit unexpectedly dramatic improvements in stability at 40° C. and 75% relative humidity, relative to alternative designs (e.g., barrier-coated famotidine multiparticulates in a matrix comprising ibuprofen). Moreover, using the design of the present invention, the barrier layer can be omitted without sacrificing stability.

"Forced degradation" conditions (e.g., 40° C. and 75% relative humidity) are used to evaluate the long-term storage stability of a pharmaceutical ingredient or composition. In general terms, a stable composition is one which comprises the pharmaceutically active ingredients in an amount, for example 95%, relative to the amount initially present in the particular composition. Stability may be determined, using forced degradation or other methods, for periods of 1 week, 1 month, 2 months, 3 months, 4 months, 5 months, 6 months, 9 months, 12 months, 15 months, 18 months, 24 months, 30 months, 36 months, longer.

Stability may also be determined by the presence and quantity of impurities. A principal degradant produced through the chemical interaction of famotidine and ibuprofen in compositions of the present invention is sulfamide. A quantitative determination of the presence of sulfamide in a unit dose form of the present invention held under forced degradation conditions for a period of time yields valuable information about the long-term stability of the composition under ordinary (e.g., room temperature) storage conditions.

Assays for evaluating the stability of a pharmaceutical composition, such as those described in the present invention, are known in the pharmaceutical arts. For example, one can determine the percentage of active pharmaceutical ingredients present in a given composition, as well as the presence and percentage of impurities, through the use of standard analytical techniques.

III. Methods of Making Tablet-in-Tablet Compositions

It is within the ability of one of ordinary skill in the art, guided by the present disclosure and with reference to the pharmaceutical literature, to prepare and manufacture unit dosage forms of the invention in accordance with the methods of the invention.

In one embodiment, the unit dosage form comprises a tablet dosage form having a famotidine core and a surrounding layer containing ibuprofen. Optionally, the tablet is coated by one or more over-coating layers, for example, to improve appearance, taste, swallowability, or for other reasons. In another embodiment, a barrier layer is interposed between the famotidine core and the ibuprofen shell. Methods for formulation and manufacture of pharmaceutical unit dose forms are known in the art, see, e.g., HANDBOOK OF PHARMACEUTCAL MANUFACTURING FORMULATIONS, 2004, Ed. Sarfaraz K Niazi, CRC Press; HANDBOOK OF PHARMACEUTCAL ADDITIVES, SECOND EDITION, 2002, compiled by Michael and Irene Ash, Synapse Books; and REMINGTON SCIENCE AND PRACTICE OF PHARMACY, 2005, David B. Troy (Editor), Lippincott Williams & Wilkins. One of ordinary skill in the art guided by this disclosure will be able to make a variety of suitable oral unit dose forms.

In general, a tablet-in-tablet composition is produced by first preparing a tablet "core" from a first component, and then applying a "shell" (e.g., through compression, or the like) of a second component in a manner such that the finished formulation comprises the core surrounded by the shell. In embodiments in which a barrier layer is interposed between the famotidine core and the ibuprofen shell, the barrier may be applied to the "core" by, e.g., spray coating, or the like.

As noted above, in some embodiments, the tablets are coated for oral administration to make the tablet easier to swallow, to mask taste, for cosmetic reasons, or for other reasons. Coating of tablets and caplets is well known in the art. Coating systems are typically mixtures of polymers, plasticisers, coloring agents and other excipients, which can be stirred into water or an organic solvent to produce a dispersion for the film coating of solid oral dosage forms such as tablets. Often, a readily soluble film is used. Materials that can be used for readily soluble films include cellulose derivatives (such as hydroxypropylmethyl cellulose) or amino-alkyl-methacrylate copolymers (e.g. Eudragit™E). Suitable coat layers, for illustration and not limitation, include Kollicoat® IR (a polyvinyl alcohol-polyethylene glycol graft copolymer) and Kollicoat IR White®, both manufactured by BASF Aktiengesellschaft (Ludwigshafen, Germany).

IV. Methods of Treatment

In one aspect, the present invention is directed to methods of treating subjects in need of ibuprofen and famotidine treatment. Methods applicable to the present invention are described in co-pending application Ser. No. 11/779,204, filed Jul. 17, 2007, and incorporated herein by reference. Subjects in need of ibuprofen and famotidine treatment include those individuals at elevated risk for developing an NSAID-induced ulcer (i.e., the subject is more susceptible than the average individual to development of an ulcer when under treatment with an NSAID). More generally, subjects in need of ibuprofen and famotidine treatment are those individuals who receive a therapeutic benefit from administration of ibuprofen and famotidine.

Ibuprofen is indicated for treatment of mild to moderate pain, dysmenorrhea, inflammation, and arthritis. In one embodiment, the subject in need of ibuprofen treatment with a dosage form of the invention is under treatment for a chronic condition. For example and without limitation, a subject in need of ibuprofen treatment may be an individual with rheumatoid arthritis, an individual with osteoarthritis, an individual suffering from chronic pain (e.g., chronic low back pain, chronic regional pain syndrome, chronic soft tissue pain), or an individual suffering from a chronic inflammatory condition. In general, a subject under treatment for a chronic condition requires ibuprofen treatment for an extended period, such as at least one month, at least four months, at least six months, or at least one year, and at least some of these subjects can benefit from receiving famotidine in combination with ibuprofen during such treatment period. In another embodiment, the subject in need of ibuprofen treatment is under treatment for a condition that is not chronic, such as acute pain, dysmenorrhea or acute inflammation and can benefit from receiving famotidine in combination with ibuprofen during such treatment.

In certain embodiments oral dosage forms of the invention are formulated so that release of both active pharmaceutical ingredients (APIs) occurs (or begins to occur) at about the same time. "At about the same time" means that release of one API begins within 5 minutes of the beginning of release of the second API, sometimes with 4 minutes, sometimes within 3 minutes, sometimes within 2 minutes, and sometimes essentially simultaneously. "At about the same time" can also mean that release of one API begins before release of the second API is completed. That is, the dosage form is not designed so that one of the APIs is released significantly later than the other API. To achieve this, combinations of excipients (which may include one or more of a binder, a lubricant, a diluent, a disintegrant, a glidant and other componants) are selected that do not substantially retard release of an API. See e.g., HANDBOOK OF PHARMACEUTICAL MANUFACTURING FORMULATIONS, 2004, Ed. Sarfaraz K Niazi, CRC Press; HANDBOOK OF PHARMACEUTICAL ADDITIVES, SECOND EDITION, 2002, compiled by Michael and Irene Ash, Synapse Books; and REMINGTON SCIENCE AND PRACTICE OF PHARMACY, 2005, David B. Troy (Editor), Lippincott Williams & Wilkins.

In the unit dose forms of the invention, both the famotidine or ibuprofen are formulated for immediate release, and not for release profiles commonly referred to as delayed release, sustained release, or controlled release. For example, in one embodiment, the unit dosage form is formulated so that famotidine and ibuprofen are released rapidly under neutral pH conditions (e.g., an aqueous solution at about pH 6.8 to about pH 7.4, e.g., pH 7.2). In this context, "rapidly" means that both APIs are significantly released into solution within 20 minutes under in vitro assay conditions. In some embodiments both APIs are significantly released into solution within 15 minutes under in vitro assay conditions. In this context, "significantly released" means that at least about 60% of the weight of the API in the unit dosage form is dissolved, or at least about 75%, or at least about 80%, or at least about 90%, and sometimes at least about 95%. In one embodiment, both famotidine and ibuprofen are at least 95% released in 30 minutes.

Dissolution rates may be determined using known methods. Generally an in vitro dissolution assay is carried out by placing the famotidine-ibuprofen unit dosage form(s) (e.g., tablet(s)) in a known volume of dissolution medium in a container with a suitable stirring device. Samples of the medium are withdrawn at various times and analyzed for dissolved active substance to determine the rate of dissolution. Dissolution may be measured, for example, as described for ibuprofen in the USP or, alternatively, as described for famotidine in the USP. Briefly, in this exemplary method, the unit dose form (e.g., tablet) is placed in a vessel of a United States Pharmacopeia dissolution apparatus II (Paddles) containing 900 ml dissolution medium at 37° C. The paddle speed is 50 RPM. Independent measurements are made for at least three (3) tablets. In one suitable in vitro assay, dissolution is measured using a neutral dissolution medium such as 50 mM potassium phosphate buffer, pH 7.2 ("neutral conditions").

Alternatively, dissolution rates may be determined under low pH conditions. Release under low pH conditions can be measured using the in vitro dissolution assay described above, but using, for example, 50 mM potassium phosphate buffer, pH 4.5, as a dissolution medium. As used in this context, the APIs are released rapidly at low pH when a substantial amount of both APIs is released into solution within 60 minutes under low pH assay conditions. In some embodiments, a substantial amount of both APIs is released into solution within 40 minutes under low pH assay conditions. In some embodiments, a substantial amount of both APIs is released into solution within 20 minutes under low pH assay conditions. In some embodiments, a substantial amount of both APIs is released into solution within 10 minutes under low pH assay conditions. In this context, a "substantial amount" means at least 15%, or at least 20%, or at least 25% of ibuprofen is dissolved and at least 80%, or at least 85%, or at least 90% of famotidine is dissolved.

In some cases, dosage forms of the present invention are designed for three times per day (TID) administration of famotidine and ibuprofen to a patient in need thereof.

When administered to avoid or mitigate the ulcerogenic effects of long-term NSAID therapy, famotidine has been administered at 40 mg BID (see Taha et al., 1996, supra). However, as described in co-pending application Ser. Nos. 11/489,275 and 11/489,705, both filed Jul. 18, 2006, and incorporated herein by reference, it has now been determined using pharmacokinetic modeling and in clinical trials, that TID administration of famotidine provides a therapeutic effect superior to that achieved by BID dosing. For example, on average, TID administration of famotidine results in intragastric pH higher than 3.5 for a greater proportion of the dosing cycle than conventional BID dosing.

Treatment using the methods of TID administration also results in reduced interpatient variability with respect to gastric pH in a population of patients receiving an ibuprofen-famotidine combination treatment. This reduction increases predictability of the treatment and reduces the likelihood that any particular patient will experience detrimental gastric pH in the course of ibuprofen-famotidine combination therapy.

Thus, in another aspect, the present invention provides a method for administration of ibuprofen to a patient in need of ibuprofen treatment by administering an oral dosage form comprising a therapeutically effective amount of ibuprofen and a therapeutically effective amount of famotidine, wherein the oral dosage form comprises a tablet-in-tablet formulation for administration three times per day (TID).

EXAMPLES

The following examples are offered to illustrate, but not to limit, the claimed invention.

Example 1

A tablet-in-tablet composition of famotidine and ibuprofen according to the present invention can be prepared by first preparing a famotidine core, which is then surrounded by an ibuprofen shell and an optional over-coating. The famotidine core is prepared by (i) combining 26.6 mg famotidine, 10.0 mg lactose monohydrate, 34.6 mg microcrystalline cellulose, 4.0 mg croscarmellose sodium, and 0.4 mg colloidal silicon dioxide in a suitably sized V-blender; (ii) mixing the combined ingredients for approximately ten minutes; (iii) discharging the blended materials from the blender and passing them through a #20 mesh screen; (iv) transferring the screened material back into the V-blender and mixing for approximately ten additional minutes; (vi) passing 1.2 mg magnesium stearate through a #30 mesh screen; (vii) adding the screened magnesium stearate to the blended material in the V-blender and mixing for approximately three additional minutes; (viii) discharging the blended material into a polyethylene lined container; and (ix) compressing the blended material into a tablet (i.e., a famotidine core) on a rotary tablet press using 0.2187" plain round SC (standard concave round) tooling. The famotidine core is then centered in a tablet-in-tablet composition by compressing 941.2 mg of Ibuprofen DC 85™ (comprises 800 mg of ibuprofen) around the famotidine core using a tablet press and 0.4100"×0.7500" oval plain tooling. The tablet-in-tablet is then preferably over-coated by placement in a suitably sized perforated coating pan to which a dispersion of Opadry II (Colorcon, Inc., West Point, Pa.) in water is added to coat the tablet-in-tablet to a weight gain of 3%.

A summary of the materials used in the tablet-in-tablet composition described in Example 1 are provided in Table 2 below.

TABLE 2

Formulation Components of Exemplary
Tablet-in-Tablet Unit Dosage Form

| Item | Material | % w/w | mg/Tab-in-Tab | Function |
|---|---|---|---|---|
| 1 | Famotidine | 2.54 | 26.6 | API |
| 2 | Lactose monohydrate (DCL 21) | 0.95 | 10.0 | Binder |
| 3 | Microcrystalline cellulose (Avicel PH102) | 3.30 | 34.6 | Binder |
| 4 | Croscarmellose sodium (Ac-di-sol) | 0.38 | 4.0 | Disintegrant |
| 5 | Colloidal silicon dioxide (Cab-o-sil M5P) | 0.04 | 0.4 | Glidant |
| 6 | Magnesium stearate | 0.11 | 1.2 | Lubricant |
| 7 | Ibuprofen granules (DC-85)* | 89.75 | 941.2 | API |

TABLE 2-continued

Formulation Components of Exemplary
Tablet-in-Tablet Unit Dosage Form

| Item | Material | % w/w | mg/Tab-in-Tab | Function |
|---|---|---|---|---|
| 8 | Opadry II (85F18422 White) | 2.93 | 30.7 | Over-coat |
| 9 | Purified Water | — | q.s. | Process aid |
| Total | — | 100.00 | 1048.7 | — |

*Contains 800 mg of ibuprofen.

Example 2

A tablet-in-tablet composition of famotidine and ibuprofen in accordance with the present invention, and which includes a barrier layer interposed between the active pharmaceutical ingredients can be prepared as described in Example 1, with the following modification. Following preparation of the famotidine core by compressing the blended material into a tablet (i.e., step (ix)), the tablet core is coated with a barrier layer by placement in a suitably sized perforated coating pan to which a dispersion of Opadry (YS-1-7003) (Colorcon) in water is added to coat the tablet core to a weight gain of 5%. With reference to the materials identified in Table 2, a weight gain of 5% requires about 3.8 mg of Opadry.

Example 3

Stability of three distinct famotidine plus ibuprofen formulations was evaluated under "forced degradation" conditions of 40° C. and 75% relative humidity to assess the viability of the different combinations of the active pharmaceutical ingredients. Surprisingly, a tablet-in-tablet formulation in accordance with the present invention exhibited remarkably improved stability, as shown in Table 3 below, as compared to both a multiparticulate formulation and a bilayer formulation, each of which relies on the presence of a barrier between the famotidine and ibuprofen to reduce chemical interaction and degradation of the active pharmaceutical ingredients.

The multiparticulate formulation comprises an ibuprofen matrix into which are dispersed a plurality of famotidine beads. Each famotidine bead consists of a microcrystalline cellulose core surrounded by a layer of famotidine which is coated with a protective barrier layer (e.g., Opadry). A description of the process of making such beads is provided in Example 9 of co-pending application Ser. No. 11/779,204, filed Jul. 17, 2007. The bilayer tablet formulation similarly comprises a layer of famotidine beads sandwiched together with a layer of ibuprofen.

As shown in Table 2, above, the tablet-in-tablet formulation in accordance with the present invention shows a markedly improved stability profile, as compared with the multiparticulate and bilayer formulations of the same chemically incompatible active ingredients, in terms of both the presence of sulfamide, the principal famotidine degradant, as well as total impurities. In the multiparticulate formulation, the issue of chemical incompatibility is addressed by the barrier layer surrounding each famotidine bead dispersed throughout the ibuprofen matrix. Similarly, in the bilayer formulation, barrier-coated famotidine beads make up the famotidine layer of the bilayer construction.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A pharmaceutical composition comprising
a first portion that comprises 800 mg ibuprofen and
a second portion that comprises 26.6 mg famotidine,
wherein the surface area of direct physical contact between ibuprofen and famotidine does not exceed 130 mm$^2$,
wherein no more than about 1% sulfamide is present when the composition is stored at 40° C. and 75% relative humidity for a period of one month,
wherein the composition is formulated so that release of both the ibuprofen and the famotidine occurs rapidly at about the same time,
wherein none of the composition, the famotidine, and the ibuprofen is enterically coated or formulated for sustained or delayed release, and
wherein the composition is for use according to a TID (three times per day) administration schedule for reducing the risk of developing ibuprofen-induced ulcers in a human patient requiring ibuprofen for an ibuprofen-responsive condition.

2. The composition of claim 1 wherein the second portion is not in direct physical contact with the first portion.

3. The composition of claim 1 wherein the second portion comprises a layer of famotidine beads.

4. The composition of claim 3 wherein each of said famotidine beads is coated with a barrier layer.

5. The composition of claim 1 wherein the second portion comprises a famotidine core and the first portion comprises an ibuprofen shell that completely surrounds the second portion with a barrier layer interposed between the first and second compartments.

TABLE 3

1 Month Stability of Famotidine + Ibuprofen Compositions
(@ 40° C. and 75% Relative Humidity)

| Stability Indicator | Multiparticulate Formulation | Bilayer Formulation | Tablet-in-Tablet Formulation (Direct Contact)† | Tablet-in-Tablet Formulation (Barrier Coated)†† |
|---|---|---|---|---|
| % Sulfamide | 3.55 | 0.91 | 0.56 | 0.00 |
| Ibuprofen Impurities** | 0.23 | 2.01 | 0.00 | 0.00 |
| Total Impurities | 4.90 | 3.00 | 0.70 | 0.00 |
| % Ibuprofen* | 100.3 | 100.5 | 99.5 | 100.8 |
| % Famotidine* | 95.5 | 103.2 | 94.6 | 96.7 |

*Calculated from initial sample assessment; each formulation includes 26.6 mg famotidine and 800 mg ibuprofen.
**Ibuprofen impurities comprise components attributable to the degradation of ibuprofen.
†Prepared according to the procedure described in Example 1.
††Prepared according to the procedure described in Example 2.

6. The composition of claim 5 wherein the core is substantially spherical in shape.

7. The composition of claim 5 wherein the core is substantially cylindrical in shape.

8. The composition of claim 1 wherein the second portion comprises a layer of famotidine and the first portion comprises a layer of ibuprofen and the two layers are separated by a barrier layer.

9. The composition of any one of claims 4, 5, and 8 wherein the barrier layer has a thickness ranging from 20 to 3,000 microns.

10. The composition of claim 9 wherein the barrier layer has a thickness ranging from about 25 to 250 microns.

11. The composition of claim 1 wherein the composition is formulated so that at least about 80% of the famotidine and at least about 80% of the ibuprofen are released from the composition into solution within 30 minutes at a pH of about 6.8 to about 7.4.

12. The composition of claim 1 wherein the release of famotidine from the composition begins within 5 minutes of the beginning of release of the ibuprofen from the composition.

13. The composition of claim 1 wherein at least 95% of the ibuprofen and the famotidine are each present when the composition is stored under room temperature storage conditions of 25° C. and 60% relative humidity for a period of nine months.

14. The composition of claim 1 wherein at least 98% of the ibuprofen and the famotidine are each present when the composition is stored under room temperature storage conditions of 25° C. and 60% relative humidity for a period of nine months.

15. The composition of claim 1 wherein the first portion completely surrounds the second portion.

16. The composition of claim 1 wherein the famotidine is not present as famotidine beads dispersed in an ibuprofen matrix.

* * * * *